United States Patent [19]
Gibson et al.

[11] Patent Number: 5,972,383
[45] Date of Patent: *Oct. 26, 1999

[54] SOLID ORALLY ADMINISTERABLE RALOXIFENE HYDROCHLORIDE PHARMACEUTICAL FORMULATION

[75] Inventors: Lowell L. Gibson, Greenwood; Kerry J. Hartauer; Julian L. Stowers, both of Indianapolis; Stephanie A. Sweetana, Bloomington; Arvind L. Thakkar, Indianapolis, all of Ind.

[73] Assignee: Eli Lilly and Company, Indianapolis, Ind.

[*] Notice: This patent is subject to a terminal disclaimer.

[21] Appl. No.: 09/088,695

[22] Filed: Jun. 1, 1998

Related U.S. Application Data

[63] Continuation of application No. 08/824,590, Mar. 26, 1997, Pat. No. 5,811,120, which is a continuation of application No. 08/479,585, Jun. 7, 1995, abandoned, which is a continuation of application No. 08/204,915, Mar. 2, 1994, abandoned.

[51] Int. Cl.$^6$ .......................... A61K 9/20; A61K 31/445
[52] U.S. Cl. .......................... 424/464; 424/451; 424/463; 424/474; 424/490; 514/962; 514/324; 514/960
[58] Field of Search .................. 424/464, 451, 424/463, 474, 490; 514/960, 962, 324

[56] References Cited

U.S. PATENT DOCUMENTS

| | | | |
|---|---|---|---|
| 4,133,814 | 1/1979 | Jones et al. | 260/326.55 |
| 4,418,068 | 11/1983 | Jones | 424/267 |
| 5,461,064 | 10/1995 | Cullinan | 514/324 |
| 5,462,950 | 10/1995 | Fontana | 514/324 |
| 5,510,370 | 4/1996 | Hock | 514/443 |

FOREIGN PATENT DOCUMENTS 2101356  1/1994  Canada.

OTHER PUBLICATIONS van Hoogdalem et al., *Pharmac. Ther.*, 44, 407 (1989).
Dissolution, Bioavailability, and Bioequivalende, (1989), Chapter 5, *Factors Affecting the Rate of Dissolution of Solid Dosage Forms*, Mack Publishing Co., PA.

*Primary Examiner*—Raj Bawa
*Attorney, Agent, or Firm*—James J. Sales

[57] ABSTRACT

This invention provides orally administerable pharmaceutical formulations comprising raloxifene, its ethers or esters, or a pharmaceutically-acceptable salt thereof, in combination with a hydrophilic carrier composition.

132 Claims, No Drawings

SOLID ORALLY ADMINISTERABLE RALOXIFENE HYDROCHLORIDE PHARMACEUTICAL FORMULATION

This application is a continuation of application Ser. No. 08/824,590 filed Mar. 26, 1997, now U.S. Pat. No. 5,811,120 issued Sep. 22, 1998 which is a continuance of application Ser. No. 08/479,585, filed Jun. 7, 1995, now abandoned, which is a file-wrapper-continuation of application Ser. No. 08/204,915, filed Mar. 2, 1994, now abandoned.

BACKGROUND

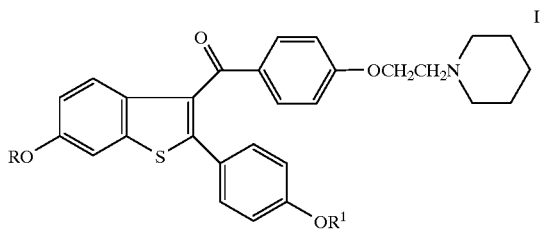

wherein R and $R^1$ are independently hydrogen, $COR^2$, or $R^3$;

$R^2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro, or tri(chloro or fluoro) methyl;

$R^3$ is $C_1$–$C_4$ alkyl, $C_5$–$C_7$ cycloalkyl, or benzyl; or a pharmaceutically-acceptable salt thereof; are nonsteriodal antiestrogens and antiandrogens. These compounds are useful in the treatment of mammary and prostatic tumors, and in the treatment of mammary and prostatic fibrocystic disease. The formula I compounds are described in U.S. Pat. No. 4,418,068 (issued Nov. 29, 1983). This patent described the preparation of these compounds, as well as their use for antiestrogen and antiandrogen therapy. The preparation of pharmaceutical compositions for antiestrogenic and antiandrogenic therapy was also described.

Raloxifene, which is 6-hydroxy-2-(4-hydroxyphenyl)-3-[4-(2-piperidinoethoxy)benzoyl]benzo[b]thiophene, is a particulary useful compound from this series of benzothiophenes. Raloxifene competitively inhibits estrogen action in a number of in vitro and in vivo models. Black, Jones, and Falcone, *Life Sci.*, 32, 1031–1036 (1983); Knecht, Tsai-Morris, and Catt, *Endocrinology*, 116, 1771–1777 (1985); and Simard and Labrie, *Mol. Cell. Endocrinology*, 39, 141–144 (1985). This compound also displays some estrogen-like actions in addition to its estrogen-antagonistic effects. Ortmann, Emons, Knuppen, and Catt, *Endocrinology*, 123, 962–968 (1988). A recent report suggests that raloxifene is useful in the treatment of osteoporosis in postmenopausal women. Turner, Sato, and Bryant, *Journal of Clinical Investigation* (In Press).

The formula I compounds may be administered as pharmaceutically-acceptable salts. A particularly useful pharmaceutically-acceptable salt of raloxifene is the hydrochloride salt. This salt form is easily prepared by the addition of hydrogen chloride to a solution of raloxifene in an organic solvent, such as tetrahydrofuran or methanol. Aqueous solubility of raloxifene hydrochloride, however, is far below what would be expected for an organic hydrochloride salt containing two phenolic hydroxyl groups. This poor solubility has somewhat limited the bioavailability of this preferred salt form. Another significant barrier to optimum and consistent absorption of raloxifene hydrochloride is its hydrophobicity.

SUMMARY OF THE INVENTION

To overcome the limited bioavailability, the present invention provides orally administerable pharmaceutical formulations comprising raloxifene, its esters or ethers, or a pharmaceutically-acceptable salt thereof, in combination with a hydrophilic carrier composition, such formulations having increased solubility in aqueous media. More particularly, the present invention provides an orally administerable pharmaceutical formulation comprising raloxifene, its esters or ethers, or a pharmaceutically-acceptable salt thereof, in combination with a surfactant, a water-soluble diluent, and optionally a hydrophilic binder. The present invention also provides pharmaceutical formulations further comprising a lubricant and a disintegrant.

DETAILED DESCRIPTION OF THE INVENTION

The present invention provides orally administerable pharmaceutical formulations comprising raloxifene, its esters or ethers, or a pharmaceutically-acceptable salt thereof, in combination with a surfactant, a water-soluble diluent, and optionally a hydrophilic binder. Raloxifene, its esters, and its ethers are represented by the following formula:

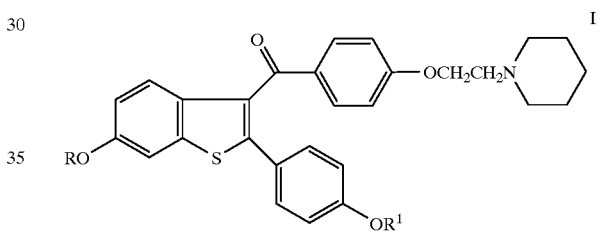

wherein R and $R^1$ are independently hydrogen, $COR^2$, or $R^3$;

$R^2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro, or tri(chloro or fluoro) methyl;

$R^3$ is $C_1$–$C_4$ alkyl, $C_5$–$C_7$ cycloalkyl, or benzyl. Raloxifene is the compound wherein R and $R^1$ are hydrogen. The preparation of this compound is described in U.S. Pat. No. 4,418,068, which is incorporated herein by reference. A pharmaceutical chemist will readily recognize that this compound can be effectively administered as an ether or ester, formed on either one or both of the phenolic hydroxyl groups. The preparation of these esters and ethers is also described in U.S. Pat. No. 4,418,068.

The general chemical terms used in the above formula have their usual meanings. The term "$C_1$–$C_{14}$ alky" represents a straight or branched alkyl chain having from one to 14 carbon atoms. Typical $C_1$–$C_{14}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, 2-methyldecyl, 2,2-dimethyldecyl, undecyl, dodecyl, and the like. The term "$C_1$–$C_{14}$ alkyl" includes within it the term "$C_1$–$C_4$ alkyl". Typical $C_1$–$C_4$ alkyl groups include methyl, ethyl, n-propyl, isopropyl, n-butyl, isobutyl, sec-butyl, and t-butyl.

The terms "$C_1$–$C_3$ chloroalkyl" and "$C_1$–$C_3$ fluoroalkyl" represent methyl, ethyl, propyl, and isopropyl substituted to any degree with chlorine or florine atoms, from one atom to full substitution. Typical $C_1$–$C_3$ chloroalkyl groups include chloromethyl, dichloromethyl, trichloromethyl, 2-chlorethyl, 2,2-dichloroethyl, 2,2,2-trichloroethyl, 1,2-dichloroethyl, 1,1,2,2-tetrachloroethyl, 1,2,2,2-tetrachloroethyl, pentachlorethyl, 3-chloropropyl, 2-chloropropyl, 3,3-dichloropropyl, 2,3-dichloropropyl, 2,2-dichloropropyl, 3,3,3-trichloropropyl, and 2,2,3,3,3-pentachloropropyl. Typical $C_1$–$C_3$ fluoroalkyl groups include fluoromethyl, difluoromethyl, trifluoromethyl, 2-fluoroethyl, 2,2-difluoroethyl, 2,2,2-trifluoroethyl, 1,2-difluoroethyl, 1,1,2,2-tetrafluoroethyl, 1,2,2,2-tetrafluoroethyl, pentafluoroethyl, 3-fluoropropyl, 2-fluoropropyl, 3,3-difluoropropyl, 2,3-difluoropropyl, 2,2-difluoropropyl, 3,3,3-trifluoropropyl, and 2,2,3,3,3-pentafluoropropyl.

The term "$C_5$–$C_7$ cycloalkyl" represents cyclic hydrocarbon groups containing from five to seven carbon atoms. The $C_5$–$C_7$ cycloalkyl groups are cyclopentyl, cyclohexyl, and cycloheptyl.

The term "$C_1$–$C_4$ alkoxy" represents groups such as methoxy, ethoxy, n-propoxy, isopropoxy, n-butoxy, t-butoxy, and the like groups.

The term "pharmaceutically-acceptable salt" represents salt forms of raloxifene, its esters, or its ethers that are physiologically suitable for pharmaceutical use. The pharmaceutically-acceptable salts can exist in conjunction with raloxifene, its esters, or its ethers as acid addition primary, secondary, tertiary, or quaternary ammonium, alkali metal, or alkaline earth metal salts. Generally, the acid addition salts are prepared by the reaction of an acid with a compound of formula I, wherein R, $R^1$, $R^2$, and $R^3$, are as defined previously. The alkali metal and alkaline earth metal salts are generally prepared by the reaction of the metal hydroxide of the desired metal salt with a compound of formula I, wherein at least one of R and $R^1$ is hydrogen.

Acids commonly employed to form such acid addition salts include organic acids such as hydrochloric, hydrobromic, hydriodic, sulfuric, and phosphoric acid, as well as organic acids such as toluenesulfonic, methanesulfonic, oxalic, para-bromophenylsulfonic, carbonic, succinic, citric, benzoic, and acetic acid, and related inorganic and organic acids. Such pharmaceutically-acceptable salts thus include sulfate, pyrosulfate, bisulfate, sulfite, bisulfite, phosphate, ammonium, monohydrogen phosphate, dihydrogen phosphate, meta-phosphate, pyrophosphate, chloride, bromide, iodide, acetate, propionate, decanoate, caprolate, acrylate, formate, isobutyrate, caprate, heptanoate, propionate, oxalate, malonate, succinate, subarate, sebacate, fumarate, hippurate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, ammonium, magnesium, tetramethylammonium, potassium, trimethylammonium, sodium, methylammonium, calcium, and the like salts.

The term "hydrophilic binder" represents binders commonly used in the formulation of pharmaceuticals, such as polyvinylpyrrolidone, polyethylene glycol, sucrose, dextrose, corn syrup, polysaccharides (including acacia, tragacanth, guar, and alginates), gelatin, and cellulose derivatives (including hydroxypropyl methylcellulose, hydroxypropyl cellulose, and sodium carboxymethylcellulose).

The term "surfactant", as used herein, represents ionic- and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, and phospholipids.

The term "water-soluble diluent" represents compounds typically used in the formulation of pharmaceuticals, such as sugars (including lactose, sucrose, and dextrose), polysaccharides (including dextrates and maltodextrin), polyols (including mannitol, xylitol, and sorbitol), and cyclodextrins.

The term "disintegrant" represents compounds such as starches, clays, celluloses, alginates, gums, cross-linked polymers (such as cross-linked polyvinylpyrrolidone and cross-linked sodium carboxymethylcellulose), sodium starch glycolate, low-substituted hydroxypropyl cellulose, and soy polysaccharides. Preferably the disintegrant is a cross-linked polymer, more preferably cross-linked polyvinylpyrrolidone.

The term "lubricant" represents compounds frequently used as lubricants or glidants in the preparation of pharmaceuticals, such as talc, magnesium stearate, calcium stearate, stearic acid, colloidal silicon dioxide, magnesium carbonate, magnesium oxide, calcium silicate, microcrystalline cellulose, starches, mineral oil, waxes, glyceryl behenate, polyethylene glycol, sodium benzoate, sodium acetate, sodium chloride, sodium laurylsulfate, sodium stearyl fumarate, and hydrogenated vegetable oils. Preferably the lubricant is magnesium stearate or stearic acid, more preferably magnesium stearate.

While all of the formulations of the present invention have increased solubility in aqueous media and, therefore, greater bioavailability would be expected, certain formulations are preferred. Preferably, the surfactant is an anionic or nonionic surfactant. Representative surfactants from this preferred group include sodium laurylsulfate, sodium docusate, ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, and diglycerides or polyoxyethylene derivatives thereof. Preferably, the water-soluble diluent is a sugar or polyol. When a hydrophilic binder is present, preferably the binder is sucrose, dextrose, corn syrup, gelatin, a cellulose derivative, or polyvinylpyrrolidone.

Certain formulations of the present invention are more preferred. More preferably, the surfactant is a nonionic surfactant, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, and diglycerides or polyoxyethylene derivatives thereof. More preferably, the water-soluble diluent is a sugar, such as lactose, sucrose, and dextrose. More preferably, the hydrophilic binder is a cellulose derivative or polyvinylpyrrolidone.

Certain formulations of the present invention are most preferred. Most preferably, the surfactant is a polyoxyethylene sorbitan fatty acid ester, such as polysorbate 80. Most preferably, the water-soluble diluent is lactose. Most preferably the hydrophilic binder, when present, is polyvinylpyrrolidone.

The orally administerable compositions of the present invention are prepared and administered according to methods well known in pharmaceutical chemistry. See Remington's Pharmaceutical Sciences, 17th ed. (A. Osol ed., 1985). For example, the compositions of the present invention may be adminstered by means of solid dosage forms such as tablets and capsules. Preferably, the compositions are formulated as tablets. These tablets are prepared by wet granulation, by dry granulation, or by direct compression.

Tablets for this invention are prepared utilizing conventional tabletting techniques. A general method of manufacture involves blending raloxifene, its ester, ether, or a salt thereof, the water-soluble diluent, and optionally a portion of a disintegrant. This blend is then granulated with a solution of the hydrophilic binder and surfactant in water and/or organic solvent, such as methanol, ethanol, isopropanol, methylene chloride, and acetone, and milled if necessary. The granules are dried and reduced to a suitable size. Any other ingredients, such as lubricants, (e.g. magnesium stearate) and additional disintegrant, are added to the granules and mixed. This mixture is then compressed into a suitable size and shape using conventional tabletting machines such as a rotary tablet press. The tablets may be film coated by techniques well known in the art.

Capsules for this invention are prepared utilizing conventional encapsulating methods. A general method of manufacture involves blending raloxifene, its ester, ether, or salt thereof, the water-soluble diluent, and optionally a portion of a disintegrant. This blend is then granulated with a solution of the hydrophilic binder and surfactant in water and/or organic solvent, and milled if necessary. The granules are dried and reduced to a suitable size. Any other ingredients, such as a lubricant (e.g. colloidal silicon dioxide) are added to the granules and mixed. The resulting mixture is then filled into a suitable size hard-shell gelatin capsule using conventional capsule-filling machines.

The following formulation examples are illustrative only and are not intended to limit the scope of the invention in any way. Tablets may be prepared using the ingredients and procedures as described below:

Formulation 1

| Ingredient | Weight (mg/tablet) |
|---|---|
| Raloxifene HCl | 200.00 |
| Polyvinylpyrrolidone | 15.75 |
| Polysorbate 80 | 5.25 |
| Lactose Anhydrous | 264.62 |
| Cross-linked polyvinylpyrrolidone | 31.50 |
| Stearic Acid | 5.25 |
| Magnesium Stearate | 2.63 |

The mixture of raloxifene HCl, lactose, and a portion of the cross-linked polyvinylpyrrolidone is granulated with an aqueous solution of the polyvinylpyrrolidone and polysorbate 80. The granules are dried, reduced to a suitable size, and mixed with stearic acid, magnesium stearate, and remaining cross-linked polyvinylpyrrolidone. The mixture is compressed into individual tablets yielding a tablet weight of 525 mg.

Formulation 2

| Ingredient | Weight (mg/tablet) |
|---|---|
| Raloxifene HCl | 200.00 |
| Polyvinylpyrrolidone | 15.75 |
| Polysorbate 80 | 5.75 |
| Lactose Anhydrous | 132.06 |
| Dextrose | 132.06 |
| Cross-linked polyvinylpyrrolidone | 31.50 |
| Stearic acid | 5.25 |
| Magnesium Stearate | 2.63 |

The mixture of raloxifene HCl, lactose anhydrous, dextrose, and a portion of the cross-linked polyvinylpyrrolidone is granulated with an alcoholic solution of polyvinylpyrrolidone and polysorbate 80. The granules are dried, reduced to a suitable size, and mixed with magnesium stearate, stearic acid, and remaining cross-linked polyvinylpyrrolidone. The mixture is compressed into individual tablets yielding a tablet weight of 525 mg.

Formulation 3

| Ingredient | Weight (mg/tablet) |
|---|---|
| Raloxifene HCl | 200.00 |
| Hydroxypropyl Cellulose | 16.00 |
| Sodium Laurylsulfate | 10.00 |
| Dextrose | 154.00 |
| Cross-linked sodium carboxymethylcellulose | 16.00 |
| Magnesium Stearate | 4.00 |

The mixture of raloxifene HCl, dextrose, and cross-linked sodium carboxymethylcellulose is granulated with an aqueous solution of hydroxypropyl cellulose and sodium laurylsulfate. The granules are dried, reduced to a suitable size, and mixed with magnesium stearate. The mixture is compressed into individual tablets yielding a tablet weight of 400 mg.

Formulation 4

| Ingredient | Weight (mg/tablet) |
|---|---|
| Raloxifene HCl | 30.00 |
| Lactose Anhydrous | 144.00 |
| Lactose, Hydrous spray Dried | 36.00 |
| Polyvinylpyrrolidone | 12.00 |
| Polysorbate 80 | 2.40 |
| Cross-linked polyvinylpyrrolidone | 14.40 |
| Magnesium Stearate | 1.20 |

The mixture of raloxifene HCl, lactose anhydrous, spray-dried hydrous lactose, and a portion of the cross-linked polyvinylpyrrolidone is granulated with an aqueous solution of polyvinylpyrrolidone and polysorbate 80. The granules are dried, reduced to a suitable size, and mixed with magnesium stearate and remaining cross-linked polyvinylpyrrolidone. The mixture is compressed into individual tablets yielding a tablet weight of 240 mg.

Formulation 5

| Ingredient | Weight (mg/tablet) |
| --- | --- |
| Raloxifene HCl | 30.00 |
| Lactose Anhydrous | 160.00 |
| Hydroxypropyl Cellulose | 11.00 |
| Poloxamer | 7.00 |
| Cross-linked sodium carboxymethylcellulose | 23.00 |
| Stearic Acid | 7.00 |
| Magnesium Stearate | 2.00 |

The mixture of raloxifene HCl, anhydrous lactose, and cross-linked sodium carboxymethylcellulose is granulated with an aqueous solution of poloxamer and hydroxypropyl cellulose. The granules are dried, reduced to a suitable size, and mixed with stearic acid and magnesium stearate. The mixture is then compressed into individual tablets yielding a tablet weight of 240 mg.

Formulation 6

| Ingredient | Weight (mg/tablet) |
| --- | --- |
| Raloxifene HCl | 30.00 |
| Lactose | 89.00 |
| Dextrose | 89.00 |
| Hydroxypropyl methylcellulose | 10.00 |
| Sodium Laurylsulfate | 5.00 |
| Cross-linked polyvinylpyrrolidone | 12.00 |
| Stearic Acid | 5.00 |

The mixture of raloxifene HCl, lactose, dextrose, and cross-linked polyvinylpyrrolidone is granulated with an aqueous solution of hydroxypropyl methylcellulose and sodium laurylsulfate. The granules are dried, reduced to a suitable size, and mixed with the stearic acid. The mixture is then compressed into individual tablets yielding a tablet weight of 240 mg.

Formulation 7

| Ingredient | Weight (mg/tablet) |
| --- | --- |
| Raloxifene HCl | 60.00 |
| Lactose Anhydrous | 156.00 |
| Polyvinylpyrrolidone | 7.20 |
| Polysorbate 80 | 7.20 |
| Cross-linked polyvinylpyrrolidone | 7.20 |
| Magnesium Stearate | 2.40 |

The mixture of raloxifene HCl lactose anhydrous, and cross-linked polyvinylpyrrolidone is granulated with an aqueous solution of polyvinylpyrrolidone and polysorbate 80. The granules are dried, reduced to a suitable size, and mixed with magnesium stearate. The mixture is then compressed into individual tablets yielding a tablet weight of 240 mg.

Formulation 8

| Ingredient | Weight (mg/tablet) |
| --- | --- |
| Raloxifene HCl | 60.00 |
| Lactose Anhydrous | 120.00 |
| Lactose, hydrous spray-dried | 30.00 |
| Polyvinylpyrrolidone | 12.00 |
| Polysorbate 80 | 2.40 |
| Cross-linked polyvinylpyrrolidone | 14.40 |
| Magnesium Stearate | 1.20 |

The mixture of raloxifene HCl, lactose anhydrous, spray-dried hydrous lactose, and a portion of the cross-linked polyvinylpyrrolidone is granulated with an aqueous solution of polyvinylpyrrolidone and polysorbate 80. The granules are dried, reduced to a suitable size, and mixed with magnesium stearate and remaining cross-linked polyvinylpyrrolidone. The mixture is then compressed into individual tablets yielding a tablet weight of 240 mg.

Formulation 9

| Ingredient | Weight (mg/tablet) |
| --- | --- |
| Raloxifene HCl | 60.00 |
| Mannitol | 77.00 |
| Dextrose | 73.00 |
| Hydroxypropyl methylcellulose | 7.00 |
| Polysorbate 80 | 4.00 |
| Sodium Starch Glycolate | 14.00 |
| Stearic Acid | 4.00 |
| Magnesium Stearate | 1.00 |

The mixture of raloxifene HCl, mannitol, dextrose, and sodium starch glycolate is granulated with an aqueous solution of polysorbate 80 and hydroxypropyl methylcellulose. The granules are dried, reduced to a suitable size, and mixed with stearic acid and magnesium stearate. The mixture is then compressed into individual tablets yielding a tablet weight of 240 mg.

Formulation 10

| Ingredient | Weight (mg/tablet) |
| --- | --- |
| Raloxifene HCl | 150.00 |
| Lactose, anhydrous | 41.00 |
| Lactose, hydrous spray dried | 10.25 |
| Polyvinylpyrrolidone | 11.50 |
| Polysorbate 80 | 2.30 |
| Cross-linked polyvinylpyrrolidone | 13.80 |
| Magnesium Stearate | 1.15 |

The mixture of raloxifene HCl, anhydrous lactose, hydrous spray-dried lactose, and a portion of the cross-linked polyvinylpyrrolidone is granulated with an aqueous solution of polyvinylpyrrolidone and polysorbate 80. The granules are dried, reduced to a suitable size, and mixed with magnesium stearate and the remaining cross-linked polyvinylpyrrolidone. The mixture is then compressed into individual tablets yielding a tablet weight of 230 mg.

Formulation 11

| Ingredient | Weight (mg/tablet) |
| --- | --- |
| Raloxifene HCl | 150.00 |
| Lactose, hydrous spray-dried | 56.00 |
| Polyvinylpyrrolidone | 7.00 |
| Polysorbate 80 | 1.20 |
| Cross-linked polyvinylpyrrolidone | 13.80 |
| Magnesium Stearate | 2.00 |

The mixture of raloxifene HCl, hydrous spray-dried lactose, and a portion of the cross-linked polyvinylpyrrolidone is granulated with an aqueous solution of polyvinylpyrrolidone and polysorbate 80. The granules are dried, reduced to a suitable size and mixed with magnesium stearate and remaining cross-linked polyvinylpyrrolidone. The mixture is then compressed into individual tablets yielding a tablet weight of 230 mg.

Formulation 12

| Ingredient | Weight (mg/tablet) |
| --- | --- |
| Raloxifene HCl | 150.00 |
| Lactose, anhydrous | 52.40 |
| Polysorbate 80 | 4.60 |
| Polyvinylpyrrolidone | 11.50 |
| Polyethylene Glycol 8000 | 11.50 |

The mixture of raloxifene HCl and anhydrous lactose is granulated with an aqueous solution of polysorbate 80 and polyvinylpyrrolidone. The granules are dried, reduced to a suitable size, and mixed with the polyethylene glycol 8000. The mixture is then compressed into individual tablets yielding a tablet weight of 230 mg.

Capsules may be prepared using the ingredients and procedures as described below:

Formulation 13

| Ingredient | Weight (mg/capsule) |
| --- | --- |
| Raloxifene HCl | 30.00 |
| Lactose, hydrous spray-dried | 178.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl, hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

Formulation 14

| Ingredient | Weight (mg/capsule) |
| --- | --- |
| Raloxifene HCl | 60.00 |
| Lactose, hydrous spray-dried | 148.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

Formulation 15

| Ingredient | Weight (mg/capsule) |
| --- | --- |
| Raloxifene HCl | 150.00 |
| Lactose, hydrous spray-dried | 58.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl, hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

We claim:

1. A method of treating mammary tumors, prostatic tumors, or osteoporosis, comprising administering to a human in need thereof a solid orally administerable pharmaceutical formulation comprising raloxifene hydrochloride in combination with a surfactant, polyvinylpyrrolidone, and a water soluble diluent, wherein:

the surfactant is a sorbitan fatty acid ester or a polyoxyethylene sorbitan fatty acid ester; and the water soluble diluent is a polyol or sugar.

2. The method of claim 1, wherein the surfactant is a polyoxyethylene sorbitan fatty acid ester.

3. The method of claim 2, wherein the surfactant is polysorbate 80.

4. The method of claim 1, wherein the water soluble diluent is a sugar.

5. The method of claim 4, wherein the surfactant is polyoxyethylene sorbitan fatty acid ester.

6. The method of claim 5, wherein the sugar is lactose.

7. The method of claim 6, wherein the surfactant is polysorbate 80.

8. The method of claim 7 further comprising a lubricant and a disintegrant.

9. The method of claim 1 further comprising a lubricant and a disintegrant.

10. The method of claim 9, wherein the lubricant is magnesium stearate or stearic acid, and the disintegrant is cross-linked polyvinylpyrrolidone.

11. The method of claim 10, wherein the surfactant is polyoxyethylene sorbitan fatty acid ester.

12. The method of claim 11, wherein the diluent is a sugar.

13. A method of treating mammary tumors, prostatic tumors, or osteoporosis, comprising administering to a human in need thereof a solid orally administerable pharmaceutical formulation consisting essentially of raloxifene hydrochloride in combination with a surfactant, polyvinylpyrrolidone, and a water soluble diluent, wherein:
the surfactant is a sorbitan fatty acid ester or a polyoxyethylene sorbitan fatty acid ester; and
the water soluble diluent is polyol or sugar.

14. The method of claim 12, wherein the surfactant is polyoxyethylene sorbitan fatty acid ester.

15. The method of claim 14, wherein the diluent is a sugar.

16. A method of treating mammary tumors, prostatic tumors, or osteoporosis, comprising administering to a human in need thereof a solid orally administerable pharmaceutical formulation consisting essentially of raloxifene hydrochloride in combination with polysorbate 80, lactose, polyvinylpyrrolidone, and magnesium stearate.

17. The method of claim 11, further comprising a film coating.

18. The method of claim 16, further comprising a film coating.

19. The method of claim 15, further comprising a film coating.

20. The method of claim 16, further comprising a film coating.

21. The method of claim 1 wherein said formulation is in the form of a tablet or capsule.

22. The method of claim 6 wherein said formulation is in the form of a tablet or capsule.

23. The method of claim 11 wherein said formulation is in the form of a tablet or capsule.

24. The method of claim 13 wherein said formulation is in the form of a tablet or capsule.

25. The method of claim 15 wherein said formulation is in the form of a tablet or capsule.

26. The method of claim 16 wherein said formulation is in the form of a tablet or capsule.

27. The method of claim 17 wherein said formulation is in the form of a tablet or capsule.

28. The method of claim 18 wherein said formulation is in the form of a tablet or capsule.

29. The method of claim 19 wherein said formulation is in the form of a tablet or capsule.

30. The method of claim 20 wherein said formulation is in the form of a tablet or capsule.

31. The method of claim 21 wherein said formulation is in the form of a tablet or capsule.

32. The method of claim 22 wherein said formulation is in the form of a tablet or capsule.

33. The method of claim 23 wherein said formulation is in the form of a tablet or capsule.

34. A method for the treatment or prophylaxis of mammary or prostatic fibrocystic disease, comprising administering to a human in need thereof a solid orally administerable pharmaceutical formulation comprising raloxifene hydrochloride in combination with a surfactant, polyvinylpyrrolidone, and a water soluble diluent, wherein:
the surfactant is a sorbitan fatty acid ester or a polyoxyethylene sorbitan fatty acid ester; and
the water soluble diluent is a polyol or sugar.

35. The method of claim 17, wherein the surfactant is a polyoxyethylene sorbitan fatty acid ester.

36. The method of claim 18, wherein the surfactant is polysorbate 80.

37. The method of claim 17, wherein the water soluble diluent is a sugar.

38. The method of claim 20, wherein the surfactant is polyoxyethylene sorbitan fatty acid ester.

39. The method of claim 21, wherein the sugar is lactose.

40. The method of claim 22, wherein the surfactant is polysorbate 80.

41. The method of claim 23 further comprising a lubricant and a disintegrant.

42. The method of claim 17 further comprising a lubricant and a disintegrant.

43. The method of claim 42, wherein the lubricant is magnesium stearate or stearic acid, and the disintegrant is cross-linked polyvinylpyrrolidone.

44. The method of claim 26, wherein the surfactant is polyoxyethylene sorbitan fatty acid ester.

45. The method of claim 44, wherein the diluent is a sugar.

46. A method for the treatment or prophylaxis of mammary or prostatic fibrocystic disease, comprising administering to a human in need thereof a solid orally administerable pharmaceutical formulation consisting essentially of raloxifene hydrochloride in combination with a surfactant, polyvinylpyrrolidone, and a water soluble diluent, wherein:
the surfactant is a sorbitan fatty acid ester or a polyoxyethylene sorbitan fatty acid ester; and
the water soluble diluent is polyol or sugar.

47. The method of claim 46, wherein the surfactant is polyoxyethylene sorbitan fatty acid ester.

48. The method of claim 30, wherein the diluent is a sugar.

49. A method for the treatment or prophylaxis of mammary or prostatic fibrocystic disease, comprising administering to a human in need thereof a solid orally administerable pharmaceutical formulation consisting essentially of raloxifene hydrochloride in combination with polysorbate 80, lactose, polyvinylpyrrolidone, and magnesium stearate.

50. The method of claim 24, further comprising a film coating.

51. The method of claim 28, further comprising a film coating.

52. The method of claim 31, further comprising a film coating.

53. The method of claim 32, further comprising a film coating.

54. The method of claim 17 wherein said formulation is in the form of a tablet or capsule.

55. The method of claim 19 wherein said formulation is in the form of a tablet or capsule.

56. The method of claim 24 wherein said formulation is in the form of a tablet or capsule.

57. The method of claim 26 wherein said formulation is in the form of a tablet or capsule.

58. The method of claim 26 wherein said formulation is in the form of a tablet or capsule.

59. The method of claim 27 wherein said formulation is in the form of a tablet or capsule.

60. The method of claim 40 wherein said formulation is in the form of a tablet or capsule.

61. The method of claim 31 wherein said formulation is in the form of a tablet or capsule.

62. The method of claim 61 wherein said formulation is in the form of a tablet or capsule.

63. The method of claim 62 wherein said formulation is in the form of a tablet or capsule.

64. The method of claim 63 wherein said formulation is in the form of a tablet or capsule.

65. The method of claim 64 wherein said formulation is in the form of a tablet or capsule.

66. The method of claim 65 wherein said formulation is in the form of a tablet or capsule.

67. A method for alleviating mammary cancer, comprising administering to a human in need thereof a solid orally administerable pharmaceutical formulation comprising raloxifene hydrochloride in combination with a surfactant, polyvinylpyrrolidone, and a water soluble diluent, wherein:
the surfactant is a sorbitan fatty acid ester or a polyoxyethylene sorbitan fatty acid ester; and
the water soluble diluent is a polyol or sugar.

68. The method of claim 67, wherein the surfactant is a polyoxyethylene sorbitan fatty acid ester.

69. The method of claim 68, wherein the surfactant is polysorbate 80.

70. The method of claim 67, wherein the water soluble diluent is a sugar.

71. The method of claim 70, wherein the surfactant is polyoxyethylene sorbitan fatty acid ester.

72. The method of claim 51, wherein the sugar is lactose.

73. The method of claim 72, wherein the surfactant is polysorbate 80.

74. The method of claim 73 further comprising a lubricant and a disintegrant.

75. The method of claim 70 further comprising a lubricant and a disintegrant.

76. The method of claim 58, wherein the lubricant is magnesium stearate or stearic acid, and the disintegrant is cross-linked polyvinylpyrrolidone.

77. The method of claim 59, wherein the surfactant is polyoxyethylene sorbitan fatty acid ester.

78. The method of claim 77, wherein the diluent is a sugar.

79. A method for alleviating mammary cancers, comprising administering to a human in need thereof a solid orally administerable pharmaceutical formulation consisting essentially of raloxifene hydrochloride in combination with a surfactant, polyvinylpyrrolidone, and a water soluble diluent, wherein:
the surfactant is a sorbitan fatty acid ester or a polyoxyethylene sorbitan fatty acid ester; and
the water soluble diluent is polyol or sugar.

80. The method of claim 79, wherein the surfactant is polyoxyethylene sorbitan fatty acid ester.

81. The method of claim 80, wherein the diluent is a sugar.

82. A method for alleviating mammary cancer, comprising administering to a human in need thereof a solid orally administerable pharmaceutical formulation consisting essentially of raloxifene hydrochloride in combination with polysorbate 80, lactose, polyvinylpyrrolidone, and magnesium stearate.

83. The method of claim 74, further comprising a film coating.

84. The method of claim 78, further comprising a film coating.

85. The method of claim 81, further comprising a film coating.

86. The method of claim 85, further comprising a film coating.

87. The method of claim 70 wherein said formulation is in the form of a tablet or capsule.

88. The method of claim 72 wherein said formulation is in the form of a tablet or capsule.

89. The method of claim 77 wherein said formulation is in the form of a tablet or capsule.

90. The method of claim 79 wherein said formulation is in the form of a tablet or capsule.

91. The method of claim 81 wherein said formulation is in the form of a tablet or capsule.

92. The method of claim 82 wherein said formulation is in the form of a tablet or capsule.

93. The method of claim 83 wherein said formulation is in the form of a tablet or capsule.

94. The method of claim 84 wherein said formulation is in the form of a tablet or capsule.

95. The method of claim 85 wherein said formulation is in the form of a tablet or capsule.

96. The method of claim 86 wherein said formulation is in the form of a tablet or capsule.

97. The method of claim 88 wherein said formulation is in the form of a tablet or capsule.

98. The method of claim 89 wherein said formulation is in the form of a tablet or capsule.

99. The method of claim 90 wherein said formulation is in the form of a tablet or capsule.

100. A method of alleviating benign prostatic hypertrophy, comprising administering to a human in need thereof a solid orally administerable pharmaceutical formulation comprising raloxifene hydrochloride in combination with a surfactant, polyvinylpyrrolidone, and a water soluble diluent, wherein:
the surfactant is a sorbitan fatty acid ester or a polyoxyethylene sorbitan fatty acid ester; and
the water soluble diluent is a polyol or sugar.

101. The method of claim 100, wherein the surfactant is a polyoxyethylene sorbitan fatty acid ester.

102. The method of claim 101, wherein the surfactant is polysorbate 80.

103. The method of claim 100, wherein the water soluble diluent is a sugar.

104. The method of claim 103, wherein the surfactant is polyoxyethylene sorbitan fatty acid ester.

105. The method of claim 104, wherein the sugar is lactose.

106. The method of claim 105, wherein the surfactant is polysorbate 80.

107. The method of claim 106 further comprising a lubricant and a disintegrant.

108. The method of claim 100 further comprising a lubricant and a disintegrant.

109. The method of claim 108, wherein the lubricant is magnesium stearate or stearic acid, and the disintegrant is cross-linked polyvinylpyrrolidone.

110. The method of claim 109, wherein the surfactant is polyoxyethylene sorbitan fatty acid ester.

111. The method of claim 110, wherein the diluent is a sugar.

112. A method of alleviating benign prostatic hypertrophy, comprising administering to a human in need thereof a solid orally administerable pharmaceutical formulation consisting essentially of raloxifene hydrochloride in combination with a surfactant, polyvinylpyrrolidone, and a water soluble diluent, wherein:
the surfactant is a sorbitan fatty acid ester or a polyoxyethylene sorbitan fatty acid ester; and
the water soluble diluent is polyol or sugar.

113. The method of claim 112, wherein the surfactant is polyoxyethylene sorbitan fatty acid ester.

114. The method of claim 113, wherein the diluent is a sugar.

115. A method of alleviating benign prostatic hypertrophy, comprising administering to a human in need thereof a solid orally administerable pharmaceutical formulation consisting essentially of raloxifene hydrochloride in combination with polysorbate 80, lactose, polyvinylpyrrolidone, and magnesium stearate.

116. The method of claim 107, further comprising a film coating.

117. The method of claim 114, further comprising a film coating.

118. The method of claim 117, further comprising a film coating.

119. The method of claim 118, further comprising a film coating.

120. The method of claim 113 wherein said formulation is in the form of a tablet or capsule.

121. The method of claim 115 wherein said formulation is in the form of a tablet or capsule.

122. The method of claim 107 wherein said formulation is in the form of a tablet or capsule.

123. The method of claim 109 wherein said formulation is in the form of a tablet or capsule.

124. The method of claim 111 wherein said formulation is in the form of a tablet or capsule.

125. The method of claim 125 wherein said formulation is in the form of a tablet or capsule.

126. The method of claim 123 wherein said formulation is in the form of a tablet or capsule.

127. The method of claim 124 wherein said formulation is in the form of a tablet or capsule.

128. The method of claim 125 wherein said formulation is in the form of a tablet or capsule.

129. The method of claim 126 wherein said formulation is in the form of a tablet or capsule.

130. The method of claim 127 wherein said formulation is in the form of a tablet or capsule.

131. The method of claim 128 wherein said formulation is in the form of a tablet or capsule.

132. The method of claim 129 wherein said formulation is in the form of a tablet or capsule.

* * * * *